United States Patent
Bosley, Jr. et al.

(10) Patent No.: US 7,951,065 B2
(45) Date of Patent: May 31, 2011

(54) TENSION FREE PELVIC FLOOR REPAIR

(75) Inventors: Rodney W. Bosley, Jr., Chester Springs, PA (US); Marvin O. Andrews, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1016 days.

(21) Appl. No.: 11/820,093

(22) Filed: Jun. 18, 2007

(65) Prior Publication Data

US 2008/0004490 A1    Jan. 3, 2008

Related U.S. Application Data

(60) Provisional application No. 60/816,783, filed on Jun. 26, 2006.

(51) Int. Cl.
*A61F 2/00* (2006.01)
(52) U.S. Cl. .......................................................... 600/29
(58) Field of Classification Search .............. 600/29–32, 600/37; 128/885; 606/153, 216
See application file for complete search history.

(56) References Cited

U.S. PATENT DOCUMENTS

| | | | |
|---|---|---|---|
| 5,899,909 A | 5/1999 | Claren et al. | |
| 5,934,283 A | 8/1999 | Willem et al. | |
| 6,010,447 A | 1/2000 | Kardjian | |
| 6,042,534 A | 3/2000 | Gellman et al. | |
| 6,206,931 B1 | 3/2001 | Cook et al. | |
| 6,241,747 B1 | 6/2001 | Ruff | |
| 6,273,852 B1 | 8/2001 | Lehe et al. | |
| 6,406,480 B1 * | 6/2002 | Beyar et al. | 606/104 |
| 2006/0229493 A1 * | 10/2006 | Weiser et al. | 600/37 |
| 2006/0252980 A1 * | 11/2006 | Arnal et al. | 600/29 |
| 2007/0021649 A1 * | 1/2007 | Nowlin et al. | 600/30 |

FOREIGN PATENT DOCUMENTS

| | | |
|---|---|---|
| WO | WO 02/078552 A1 | 10/2002 |
| WO | WO 2003/092546 A3 | 11/2003 |
| WO | WO 2007/002071 A1 | 1/2007 |

OTHER PUBLICATIONS

International Search Report for International Application No. PCT/US2007/014174, dated Dec. 21, 2007, 4 pages.
Written Opinion of the International Searching Authority for International Application No. PCT/US2007/014174, dated Dec. 21, 2007, 6 pages.
International Preliminary Report on Patentability dated Jan. 15, 2009 for related PCT/US2007/014174.

* cited by examiner

*Primary Examiner* — Charles A Marmor, II
*Assistant Examiner* — Christine D Hopkins
(74) *Attorney, Agent, or Firm* — Brinks Hofer Gilson & Lione

(57) ABSTRACT

A kit and method for supporting a pelvic floor of a person with stress urinary incontinence or other symptoms. The method involves using barbed sutures as part of a sling for supporting the pelvic floor or urethra of a person experiencing stress urinary incontinence or other symptoms. A surgeon implants the sling along with the barbed sutures, using one of several known methods. The barbed sutures may be interwoven with the sling and the supports for the sling, so that once the sling and its supports are placed into the patient, barbs of the sutures will resist movement. The sutures may also be woven into the supports to resist movement.

6 Claims, 4 Drawing Sheets

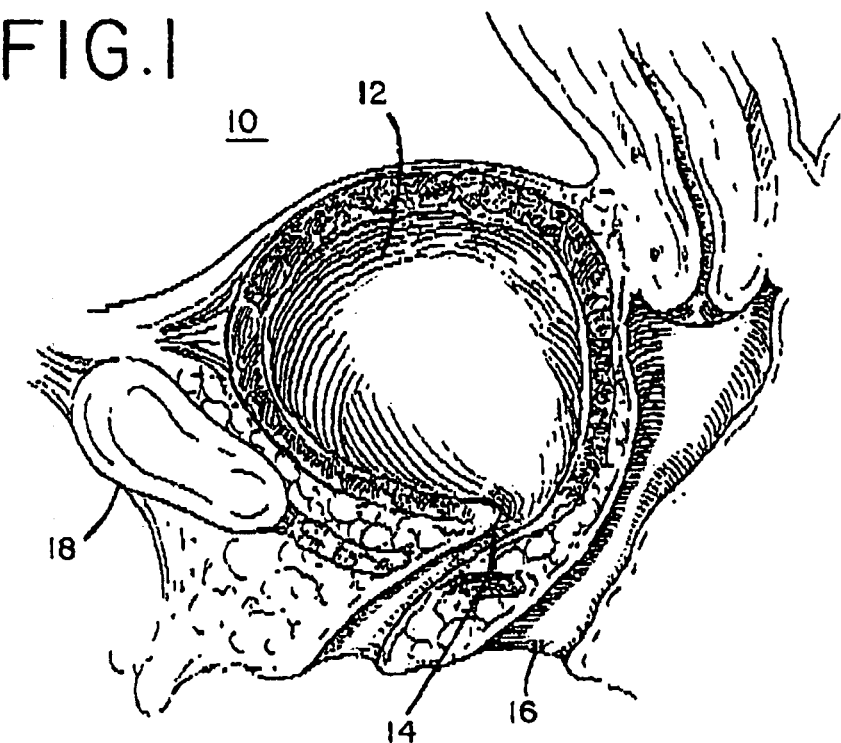
FIG. 1
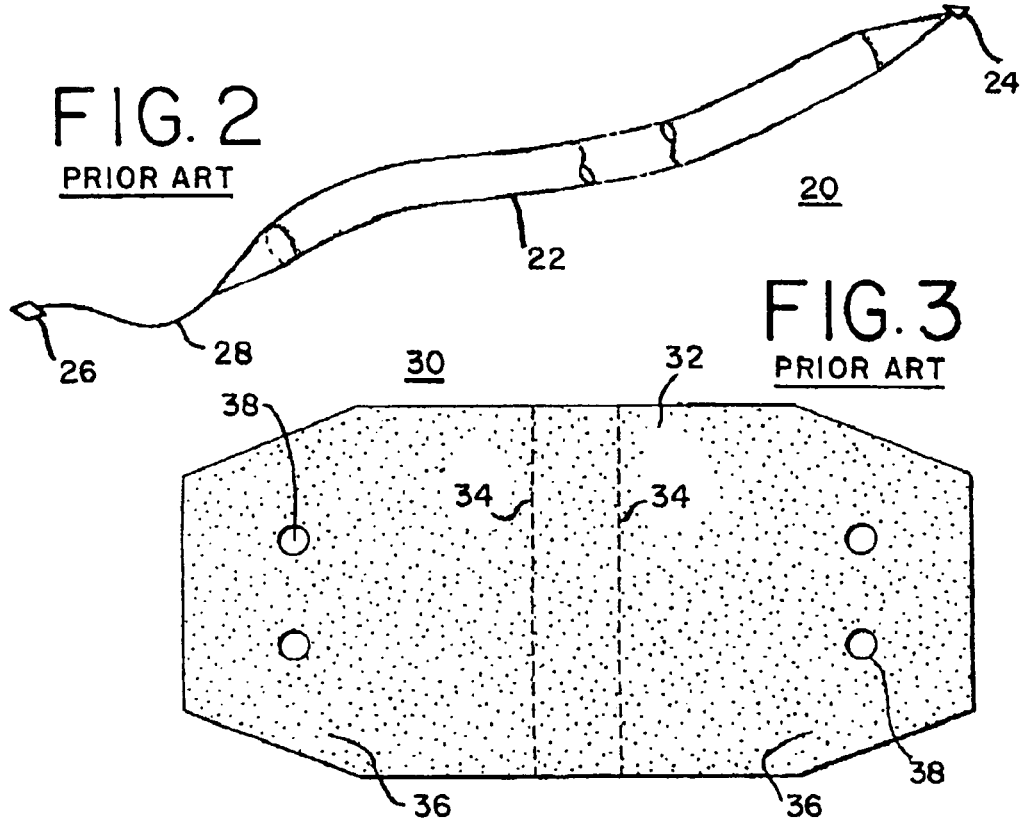
FIG. 2 PRIOR ART
FIG. 3 PRIOR ART

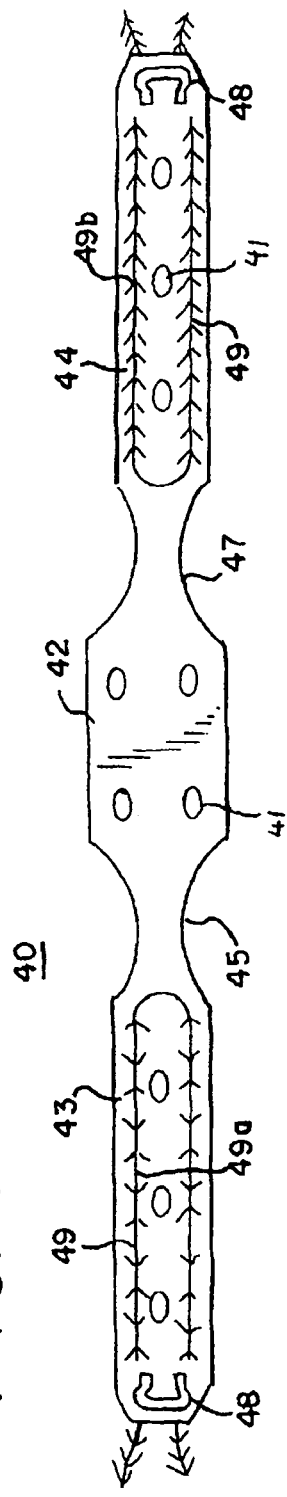
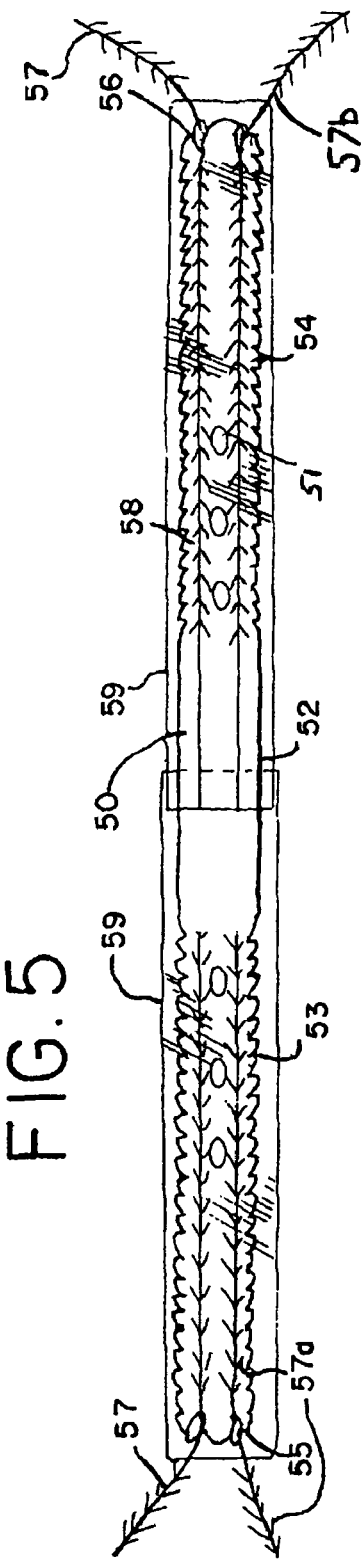

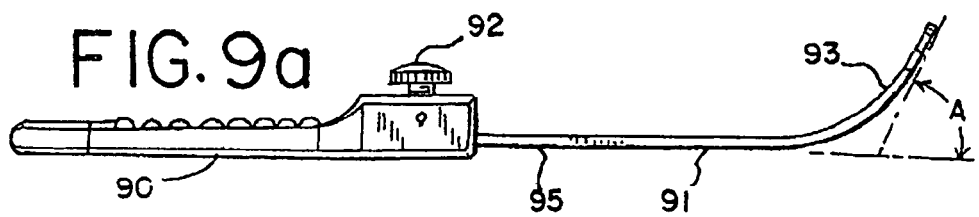
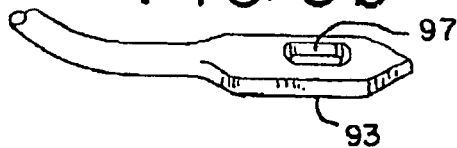
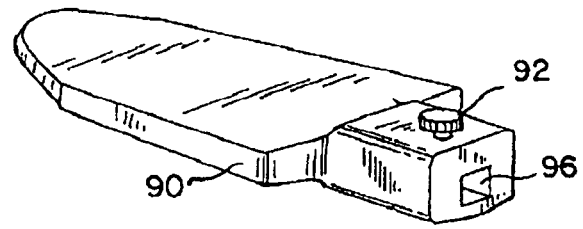
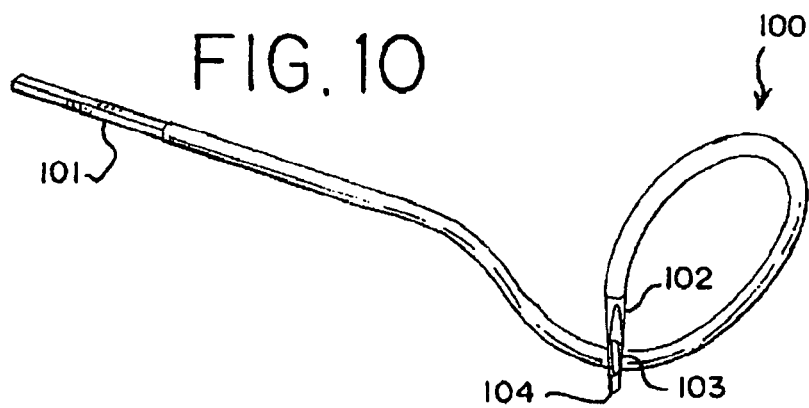

TENSION FREE PELVIC FLOOR REPAIR

RELATED APPLICATIONS

The present patent document claims the benefit of the filing date under 35 U.S.C. §119(e) of Provisional U.S. Patent Application Ser. No. 60/816,783, filed Jun. 26, 2006, which is hereby incorporated by reference in its entirety.

FIELD OF THE INVENTION

This invention relates to the treatment of urinary incontinence.

BACKGROUND OF THE INVENTION

Urinary incontinence, arising from several conditions, is a common symptom in many women, especially women who had previous vaginal deliveries. Stress urinary incontinence (SUI) is the involuntary loss of urine due to increases in intra-abdominal pressure associated with laughing, lifting, coughing, or other physical activity. SUI may be caused by excessive bladder neck mobility (hypermobility) and/or intrinsic sphincter deficiency (ISD). Bladder neck hypermobility is typically the result of weak periurethral and bladder support tissue which permits the movement of the bladder neck and proximal urethra during times of increased intra-abdominal pressure. ISD is an inherent weakness of the internal urinary sphincter due to scarring or denervation which renders the internal urinary sphincter incompetent. An incompetent urinary sphincter may allow SUI in the absence of bladder neck hypermobility as urine is pushed through the incompetent sphincter with increases in intra-abdominal pressure. Some patients have both bladder neck hypermobility and ISD resulting in extreme SUI. It is important to recognize and understand that SUI is a symptom, not a disease or disorder per se.

A variety of techniques has arisen for treating the symptom of SUI. The techniques primarily involve supporting the urethra in a position where the flow of urine may be controlled by urethral compression during increases in intra-abdominal pressure. FIG. 1 illustrates the problem. Internal parts 10 of a female include a bladder 12 and a urethra 14 leading from the bladder. The urethra is a relatively small tubular organ leading from the bladder to the external portion of the body. FIG. 1 also illustrates the pubic bone 18 and the vagina 16. The urethra is shown in a relatively unsupported position, slumped to the right in FIG. 1, where the urethral sphincter may be unable to control the flow of urine in the patient.

Prior art techniques include a variety of ways to support the urethra. These ways include suturing to musculature or fascia beneath the urethra. Perhaps the most popular recent methods have involved placing a sling or hammock beneath the urethra, and supporting the hammock by anchoring it to fascia or other suitable supports, such as rectus muscle, the pubic bone, Cooper's ligament, or to subcutaneous tissue above the rectus fascia. Prior art slings are depicted in FIGS. 2 and 3. In FIG. 2, a prior art sling 20 includes a central portion 22 and means for attaching 24, 26 on the ends of the sling. These means for attaching may include tabs as shown or may include a suture 28 to allow a surgeon to draw the ends of the sling through the patient. FIG. 3 depicts another prior art sling 30. This sling has a central portion 32 with visual indicators 34 to aid the surgeon in positioning the sling under the urethra. The sling may be tapered towards the ends 36, and also has suture receiving sites 38 to resist tearing as the surgeon extends the sling through the body of the patient. Certain of these materials are disclosed in U.S. Pat. Nos. 6,042,534, and in 5,934,283 and 6,010,447, all incorporated herein by reference in their entirety. These techniques may involve anchoring to the pubic bone and may be objectionable to the patient. Other techniques for implantation with loose tapes are numerous in the prior art, including U.S. Pat. Nos. 5,899,909 and 6,273,852, incorporated herein by reference in their entirety.

These prior art techniques have disadvantages in that they are not necessarily stable within the body of the patient. That is, once the sling is placed under the urethra or within tissues of the pelvic floor, the sling may tend to move, and thus the patient does not receive the benefit of the surgeon's precise placement of the sling for supporting the pelvic floor or the urethra, and gaining the best control over incontinence. Other disadvantages lie in the design of the sling itself. Since at least the central portion of the sling has a constant width, it may be subject to rolling or bunching under the urethra. This may tend to re-form a wide band into a narrow supporting band underneath the urethra, providing less support and possibly cutting into the urethra in extreme cases.

What is needed are improved or alternative slings or hammocks for urethral support. What is needed are slings that will remain where the surgeon places them, and which will gently and reliably support the urethra and potentially other tissue structures, allowing a patient long-term relief from stress urinary incontinence.

BRIEF SUMMARY OF THE INVENTION

The present invention is directed to kits and methods for installing a sling for supporting a pelvic floor or for supporting a urethra. One aspect of the invention is a method of supporting a pelvic floor. The method comprises creating a pathway for a supporting structure in a pelvic floor, placing a supporting structure in the pelvic floor, and supporting the structure within the pathway barbed sutures.

Another aspect of the invention is a kit for repairing a pelvic floor. The kit comprises a support for placement within tissues of the pelvic floor, the support comprising a central portion, two end portions, and two transition portions connecting the central portion with the two end portions, and at least one length of barbed suture woven into the support for securing the support in the tissues.

Another aspect of the invention is a kit for treating urinary incontinence. The kit includes a support for placement adjacent a urethra, the support including at least one layer of a fabric-like material; and a length of barbed suture, the length secured to the support by a plurality of barbs from the barbed suture, wherein the support is secured within a patient by at least a portion of the length.

There are many ways to practice the present invention, as shown in the following drawings and specification. The embodiments are not meant to limit the invention, but rather to describe and illustrate the many ways that the present invention may be used.

BRIEF DESCRIPTION OF SEVERAL VIEWS OF THE DRAWINGS

FIG. 1 depicts a problem urethra requiring support.

FIG. 2 represents a prior art sling for supporting a urethra.

FIG. 3 represents another prior art sling for supporting a urethra.

FIG. 4 is a plan drawing depicting a first embodiment of a urethral support sling with barbed sutures.

FIG. 5 is a plan view of a second embodiment of a urethral support sling with barbed sutures.

FIGS. 9a-9c depict a needle for installing a sling according to the present invention.

FIG. 10 depicts a helical needle for installing a sling according to the present invention.

DETAILED DESCRIPTION OF THE INVENTION

Figure 6:
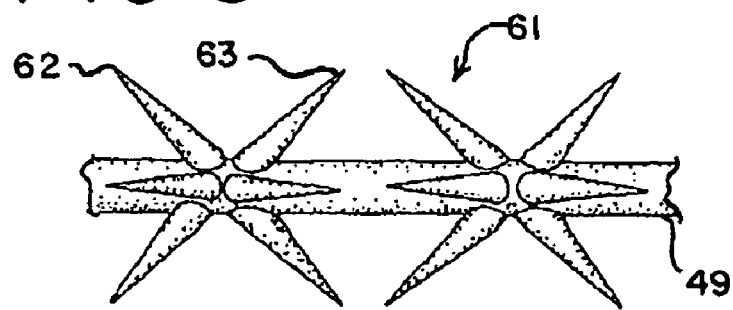
FIGS. 6-8 are perspective views of sutures with barbs.

The present invention provides slings with adaptations for ameliorating potential causes of movement or pull-out of a sling, in addition to the problem of rollover. In some cases, the problem of roll-over may be related to the support portion of the sling, since the primary consideration of this portion in most cases is to provide support for about 1-2 cm of the urethra, spreading the mechanical load and avoiding a stress concentration whereby the sling could damage the urethra.

At least one contributor to roll-over forces and roll-over may be the endopelvic fascia, running near the urethra and roughly perpendicular to the sling. The sling may be implanted near the fascia, where the bulk and stiffness of the endopelvic fascia may interfere with a flat, planar installation of the sling by compressing the sling where the fascia pass through the sling. The sling may then be rolled or bunched into a narrow band under the urethra, depriving the urethra of broader, less stressful support.

When a sling is placed in a patient to support a urethra, the sling may be placed directly adjacent the urethra, i.e., in direct contact with the urethra, or the sling may be placed so as to support the urethra indirectly, e.g., with one or more layers of fascia or other tissue between the sling and the urethra, as desired by the physician. Either technique is referred to as "adjacent" the urethra, whether or not the sling directly supports the urethra.

To facilitate addressing this problem, embodiments of the present invention provide relief, or a recess, near the support portion of the sling, as well as barbed sutures to prevent movement or pull-out of the sling. The relief features may provide a relief for any endopelvic fascia passing transversely to the orientation of the sling when implanted. Narrowing transitions for providing relief are preferably gently radiused so that the sling continues to provide maximum support for the urethra. The transitions are preferably narrower than the adjacent support portion and the left or right side "tail" or supporting portion of the sling.

In addition to or as an alternative to narrower portions, relief may be effectively provided by modifying material in the relief area to render it less resistant to deformation or displacement by surrounding patient tissues. For example, material in the relief area may be windowed, sliced, perforated, or otherwise sufficiently weakened or otherwise modified to facilitate the passage of endopelvic fascia without curling or rolling the intermediate portion of the sling device.

Other features besides barbed sutures may be added to the sling to increase resistance to pull out. For example, anchors may provide resistive or convoluted surfaces, surfaces that interfere with movement of the sling, thus increasing resistance to pullout or movement, as depicted in co-pending application Ser. No. 10/427,394. These features or anchors may also include protuberances such as barbs, whereby the sling itself, as well as the sutures, is provided with a plurality of small anchors to prevent movement once the sling is placed into a patient. In addition, or instead of barbs or protuberances, the sling may be provided with serrations on its edges, in order to resist pullout.

Other features that may help in anchoring the sling include perforations in the sling, in the support portions or in the transition regions, or both. Some of these anchoring features, especially penetrations or perforations, may also help to encourage the in growth of bodily tissue into the sling, thus supporting and stabilizing the sling. These features may help to stabilize the sling within the patient by increasing the surface area that opposes movement within the patient's body.

FIG. 4 depicts an improved sling 40, having a support portion 42, first (left) and second (right) portions 43, 44, and transitions 45, 47 where the support portion connects to the first and second portions. In a preferred embodiment, the sling may be about 1.5 to 2 cm wide in the support portion. Other embodiments may have a width from about 8 mm to much wider if the sling is meant to support a bladder as well as a urethra. In those embodiments, the sling may be as wide as 7 cm, and the support portion may be about 4 cm long. The transitions should be smoothly radiused so as not to provide sites for initiation of tears or cracks in the material. In one embodiment, the transitions may have a radius of about 2 cm, and the narrowest portion of the sling may occur in the radiused portion, the sling being as narrow as 7-8 mm at that point. One or more tangs 48 may also be sewn or molded into the sling for ease of manipulating with a needle or other surgical instrument. As described above, sling 40 may also have penetrations 41 to encourage in growth into the patient. In addition, the sling may have a treatment of one or more drugs impregnated into the sling. The drug or drugs may be prophylactic, such as to prevent infection or rejection, or they may be present for a therapeutic reason.

In this embodiment, barbed sutures 49 are woven or sewn into sling 40 itself, as shown. Barbed sutures 49 may comprise two lengths of sutures as shown, or may be a single looped suture, or may include more than two lengths. As shown in FIG. 4, the sutures may extend only part of the length of the sling, weaving in and out as desired, so that the barbs may anchor themselves to the ends. Barbed suture 49 may includes barbs 49a facing more than one direction, or may include barbs 49b facing in a single direction. In addition, barbed sutures 49 may be used to attach the sling to the fascia or tissue of a patient.

Barb structures useful in embodiments of the present invention are described in several places. One description is given in U.S. Pat. No. 6,241,747, for a barbed bodily tissue connector, incorporated herein by reference in its entirety. The barbs are placed on the surface of the connector to become embedded in the patient, and to help close a wound or an incision. In at least some applications, the barbed connector is intended as the primary closure means for the incision. The barbs typically have a diameter less than the diameter of the connector, or in this case, the diameter of the suture. The diameter of the barb varies, and the barb may be in a roughly conical shape, with the larger end on the suture, tapering to a sharp point at the opposite end of the barb.

The barb is also angled one way or another, typically at an acute angle to the suture, so that the suture may be pulled one way through the sling, but will resist being pulled in the opposite way. The barbs may be arranged as desired along the length of the suture. For instance, they may be placed in a helical pattern, or they may be varied as desired. They may be placed in two or more rows, staggered along the length of the suture, or they may be placed in a more random pattern.

The suture may be made from a suitable collagenous materials including, but are not limited to, purified or reconstituted collagen; bovine or other mammalian pericardium; decellularized dermis; submucosa tissue such as urinary bladder submucosa, stomach submucosa, small intestine submucosa, and uterine submucosa; serosa tissue such as bovine serosa; basement membrane tissue such as liver basement membrane; autologous, allogenic or xenogenic fascia lata; and so on. Materials which constitute a collagen-based extracellular matrix (ECM) are preferred, but not required. In general, mammalian tela submucosa tissues, which are collagen based and thus predominantly collagen, are preferred ECM materials. These tissues may be procured from the alimentary, respiratory, urinary or genital tracts of animals.

ECM materials, when used, may optionally retain growth factors or other bioactive components native to the source tissue. For example, the submucosa tissue may include one or more growth factors such as basic fibroblast growth factor (FGF-2), transforming growth factor beta (TGF-beta), epidermal growth factor (EGF), and/or platelet derived growth factor (PDGF). As well, submucosa tissue used in the invention may include other biological materials such as heparin, heparin sulfate, hyaluronic acid, fibronectin and the like.

Another suture material is small intestine submucosa (SIS) obtained from a porcine source, although the material for the suture is not limited to this material. Cross-linked ECM materials are one embodiment of materials useful in the present invention, as are materials that are not cross-linked. Cross-linked materials tend to be less bioresorbable than non-cross linked materials.

A suture may also be formed from a tissue engineered product involving cell culture techniques, such as the use of stem cell technology or using smooth muscle cells with SIS material. One such technique is to seed smooth muscle cells onto SIS material or other biodegradable scaffold. Other biodegradable scaffolds, some of which are mentioned elsewhere, include polyglycolic acid (PGA), collagen, and extracellular matrix materials (ECM), as well as SIS. A suture may also be formed using stem cell technology. One technique is to culture stem cells in a specific medium to induce smooth muscle differentiation. Suitable media include, but are not limited to, SIS, ECM, PGA, and collagen. The new derived cells, formed from Stem cells, could be formed into the product or seeded onto the matrix material to form a sling.

Collagenous materials used for sutures may be cross-linked with a chemical cross-linking agent, such as formaldehyde or glutaraldehyde. Other cross-linking agents that may be used include, but are not limited to aldehydes, sulfo-N-hydroxysuccinimide, polyepoxy compounds, and carbodi-imides, including 1-ethyl-3-(3-dimethylaminopropyl) carbodiimide hydrochloride (EDC). Polyepoxy compounds may include, but are not limited to glycol diglycidyl ether, polyol polyglycidyl ether, and dicarboxylic acid diglycidyl ester.

Materials for sutures may also be cross-linked by radiation treatment, such as exposure to electron-beam radiation. In some instances, the strength or stiffness may in some ways be degraded by the use of electron-beam radiation. The degree of support or reinforcement necessary may determine the material used. The cross-linking lends additional strength and stiffness to materials, better enabling them to carry loads and absorb stresses. In other applications, non-cross-linked materials may suffice, and their greater flexibility and resilience may serve the patient better than a stronger, stiffer material. In addition, non-cross-linked, more bioresorbable materials are very useful in embodiments of sutures useful for implantation within a human body. Sutures made from any of these or other materials may also be coated with an antibacterial or an anti-inflammatory treatment to reduce infection or inflammation at the implanted sites. Sutures may also be coated with a protease inhibitor to enhance tissue regeneration.

In addition to and potentially in combination with these natural materials, other natural or synthetic materials may be useful as sutures. These materials may include, but are not limited to, monofilament polyester or braided multi-filament polyester, nylon, polyaramid, polypropylene, polyethylene, polyesters, polystyrene, polyacrylates, polyvinyl compounds such as polyvinyl chloride, polycarbonates, polytetrafluoroethylene, thermanox, nitrocellulose, cotton, polyglycolic acid, cat gut sutures, cellulose, gelatin, dextran, and the like. In some cases, bioresorbable materials may be indicated. Bioresorbable materials are those which ideally disappear after treatment without leaving a trace of their prior presence. Bioresorbable materials which may be used alone or in conjunction with ECM materials include, but are not limited to, biodegradable polyesters, polyorthoesters, polyglycolide-co-lactides, polyanhydrides, polyesteramides, polyglycolic acid, polylactide, polycaprolactone, and polydioxanone. Co-polymers of glycolic and lactic acid, such as poly(d,l-lactic-co-glycolic) acid (PLGA), may also be used The sutures may be made by any of these materials, or by a combination of these materials.

Another embodiment features the serrations discussed above as well as barbed sutures extending the length of the sling. FIG. 5 depicts an improved sling 50 having an intermediate portion 52, first (left) and second (right) portions 53, 54, with serrations 58 on both the left and the right portions. Sling 50 also has left and right ends 55, 56, and barbed sutures 57 woven through the sling to aid to implanting and immobilizing the sling in the body of a patient. In this embodiment, barbs 57a face one way on the first or left side 53 of the sling and an opposite way 57b on the second or right 54 side of the sling. In some embodiments, the sling may be from about 10 mm wide to about 18 mm wide. The serrations may be molded into the material when it is prepared, or the serrations may be added by secondary machining or forming operations performed on the sling. Penetrations or holes 51 may also be added to encourage stability and in growth into the patient. The sling may be enclosed in one or more plastic sheaths 59 to ensure sterility and, in some instances, to facilitate travel of the sling through the body of the patient.

Figure 7:
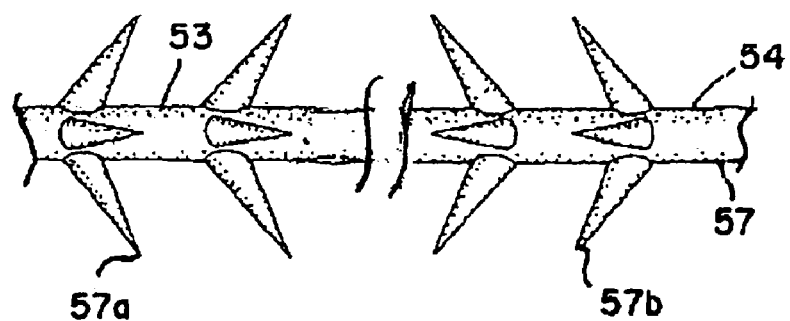
Figure 8:
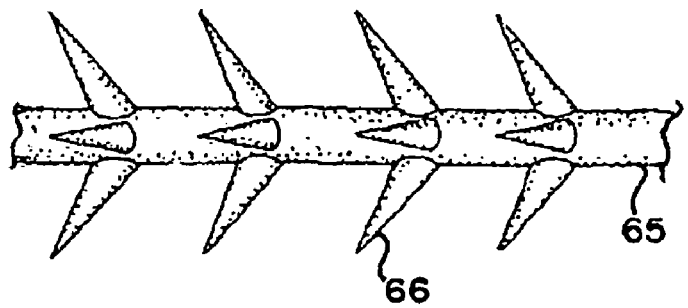

FIGS. 6-8 depict the sutures in detail. In FIG. 6, suture 49 has barb clusters 61 with barbs 62 facing one direction for resisting pullout in a first direction. Clusters 61 also include barbs 63 facing a different direction and resisting pull-out from an opposite direction. Suture 57 in FIG. 7 does not have clusters of barbs facing two directions, but does have barbs 57a on first or left side 53 facing in one direction, and barbs 57b on second or right side 54 facing a different direction. In FIG. 7, left side 53 may be pulled to the left, but will resist being pulled to the right. Right side 54 may be pulled to the right, but will resist being pulled to the left. Another embodiment of a suture with barbs is depicted in FIG. 8. Shown is suture 65 with barbs 66, all facing in roughly a single direction, in this embodiment facing left, so that suture 65 will resist pullout to the left, while the suture may be pulled to the right.

Slings according to the present invention may be placed into a patient in one of several ways. Retrograde and antegrade placement procedures both involve vaginal placement with tiny abdominal incisions to which the surgeon advances the support sections of the sling. The surgeon then adjusts the sling before trimming the sling just under the abdominal skin. Transobturator placement procedures involve advancing the sling and its support sections, and then suturing the sling to the transobturator ligament. An alternate procedure involves advancing the supports further, on the left and right side, through the obturator foramina, and then through tiny incisions in the thigh (groin), thus avoiding placement in the region of the bladder or the abdomen.

Needles may used to implant the sling embodiments according to the present invention into a patient. FIGS. 9a-9c and FIG. 10 depict needles and handles useful as part of the kits for the present invention. FIG. 9a depicts a side view of a handle 90 assembled with needle 91 for implanting a sling according to a retrograde or antegrade procedure. The sling may be used as a part of a kit furnished to a surgeon for inserting the sling into the body of a patient. The components may include, a handle 90 for grasping by the surgeon, and a set-screw 92 for securing needle 91 into the handle.

The needle may have a proximal end 95 for securing into the handle by means of flats on the proximal end of the needle. As shown in FIG. 9b, needle 91 also has a distal end 93 with an aperture 97 for attaching the sling to the needle. The distal end 93 may also be flattened to more easily attach the sling to the needle. As shown in FIG. 9c, handle 90 has an orifice 96 for accepting the proximal end of the needle. The set screw 92 is then used to snug the needle to the handle, preventing movement and rotation once the set screw is hand-tightened. The set screw may be made of metal or plastic. A needle tight and secure in the handle gives the surgeon a steady grip as the needle is used to implant the sling. The kit may also include a second needle, requiring cystoscopy to be performed only once during the implanting procedure.

The needle used may be a modified Stamey needle used as a ligature carrier, preferably having a curved portion. The curve is from about 50 degrees to about 75 degrees, shown in FIG. 9a as angle A. As mentioned above, a portion of the proximal end of the needle is flattened to fit into the handle, which has a rectangular aperture for receiving the needle. A portion of the distal end of the needle may also be flattened, and may have an aperture for attaching a suture or for directly attaching the sling. The sling may be directly attached if there is a tang or other attaching feature on the sling for inserting into the aperture in the distal end of the needle. Other ligature carriers may also be used, whether or not a suture is used to connect the sling to the needle.

As shown in FIG. 10, a helical needle 100 may also be used to place a sling, using a transobturator approach. Helical needle 100 may have a left-handed twist as shown, with a proximal end 101 suitable for secure placement into a handle, and a distal end 102. Distal end 102 preferably has an eye 103 for placing a suture for guiding placement of a sling. Distal end 102 also preferably has a sharp-pointed end 104, for helping to develop the space for placement of the sling and the sutures according to the transobturator method. Helical needles preferably come in pairs, one needle with a left-handed twist and one needle with a right-handed twist for ease of placement of a support sling on either side of the urethra.

The barbed sutures and kits of the present invention help achieve lasting placement of the sling, because once the sling is placed, it tends naturally to stay in place. Even if all the barbs on one side of the sling face only one direction, and the barbs on the other side face the other way, the sling will resist movement in either longitudinal direction. If the barbs are also spaced about the circumference of the suture, they will tend to resist movement in other directions as well.

Attention has focused on urethral applications for these materials, particularly for female patients. As noted above, slings made from these materials may also be used on male patients, particularly males experiencing urinary disfunction after prostate surgery or other trauma to the urethral region. The slings made from these materials are not limited to supporting the urethra and the bladder, but may also be used for supporting a variety of soft tissues within the body. Slings made from these materials may be used for repair of a rectum or for paravaginal repairs, such as vault prolapse, cystocele, and enterocele. Abdominal walls may use these materials, as well as herniated tissues, prolapsed tissues, and perforated tissues. Suitable applications for herniated tissues may include abdominal, inguinal, diaphragmatic, epigastric, gastroesophegeal, hiatal, intermuscular, mesenteric, paraperitoneal, rectovaginal, uterine and vesical. These materials may also be used for general tissue repair in areas such as an anterior pelvic floor, bladder repair, thoracic walls, and the like.

The sling may be made from any suitable material. Suitable collagenous materials include, but are not limited to, purified or reconstituted collagen; bovine or other mammalian pericardium; decellularized dermis; submucosa tissue such as urinary bladder submucosa, stomach submucosa, small intestine submucosa, and uterine submucosa; serosa tissue such as bovine serosa; basement membrane tissue such as liver basement membrane; autologous, allogenic or xenogenic fascia lata; and so on. Materials which constitute a collagen-based extracellular matrix (ECM) are preferred. In general, mammalian tela submucosa tissues, which are collagen based and thus predominantly collagen, are preferred ECM materials. These tissues may be procured from the alimentary, respiratory, urinary or genital tracts of animals.

ECM materials, when used, may optionally retain growth factors or other bioactive components native to the source tissue. For example, the submucosa tissue may include one or more growth factors such as basic fibroblast growth factor (FGF-2), transforming growth factor beta (TGF-beta), epidermal growth factor (EGF), and/or platelet derived growth factor (PDGF). As well, submucosa tissue used in the invention may include other biological materials such as heparin, heparin sulfate, hyaluronic acid, fibronectin and the like.

A preferred material is small intestine submucosa (SIS) obtained from a porcine source, although the material for the sling is not limited to this material. As mentioned above, other materials useful in slings according to the present invention are disclosed in U.S. Pat. No. 6,206,931, hereby incorporated by reference in its entirety. Cross-linked ECM materials are one embodiment of materials useful in the present invention, as are materials that are not cross-linked. Cross-linked materials tend to be less bioresorbable than non-cross linked materials.

A sling may also be formed from a tissue engineered product involving cell culture techniques, such as the use of stem cell technology or using smooth muscle cells with SIS material. One such technique is to seed smooth muscle cells onto SIS material or other biodegradable scaffold. Other biodegradable scaffolds, some of which are mentioned elsewhere, include polyglycolic acid (PGA), collagen, and extra-cellular matrix materials (ECM), as well as SIS. A sling may also be formed using stem cell technology. One technique is to culture stem cells in a specific medium to induce smooth muscle differentiation. Suitable media include, but are not limited to, SIS, ECM, PGA, and collagen. The new derived cells, formed from Stem cells, could be formed into the product or seeded onto the matrix material to form a sling.

Collagenous materials used for slings may be cross-linked with a chemical cross-linking agent, such as formaldehyde or glutaraldehyde. Other cross-linking agents that may be used include, but are not limited to aldehydes, sulfo-N-hydroxysuccinimide, polyepoxy compounds, and carbo-diimides, including 1-ethyl-3-(3-dimethylaminopropyl) carbodiimide hydrochloride (EDC). Polyepoxy compounds may include, but are not limited to glycol diglycidyl ether, polyol polyglycidyl ether, and dicarboxylic acid diglycidyl ester.

Materials for slings may also be cross-linked by radiation treatment, such as exposure to electron-beam radiation. In some instances, the strength or stiffness may in some ways be degraded by the use of electron-beam radiation. The degree of support or reinforcement necessary may determine the material used. The cross-linking lends additional strength and stiffness to materials, better enabling them to carry loads and absorb stresses. In other applications, non-cross-linked materials may suffice, and their greater flexibility and resilience may serve the patient better than a stronger, stiffer material. In addition, non-cross-linked, more bioresorbable materials are very useful in embodiments of slings useful for implantation within a human body. Slings made from any of these or other materials may also be coated with an antibacterial or an anti-inflammatory treatment to reduce infection or inflammation at the implanted sites. Slings may also be coated with a protease inhibitor to enhance tissue regeneration.

In addition to and potentially in combination with these natural materials, other natural or synthetic materials may be useful as slings or as reinforcements or additions to slings. These materials may include, but are not limited to, nylons, polyesters, polystyrene, polyethylene, polypropylene, polyacrylates, polyvinyl compounds such as polyvinyl chloride, polycarbonates, polytetrafluoroethylene, thermanox, nitrocellulose, cotton, polyglycolic acid, cat gut sutures, cellulose, gelatin, dextran, and the like. In some cases, bioresorbable materials may be indicated. Bioresorbable materials are those which ideally disappear after treatment without leaving a trace of their prior presence. Bioresorbable materials which may be used alone or in conjunction with ECM materials include, but are not limited to, biodegradable polyesters, polyorthoesters, polyglycolide-co-lactides, polyanhydrides, and polyesteramides. The slings for supporting soft tissues within the body may be made by any of these materials, or by a combination of these materials.

The sling embodiments of the present invention may be made from one or more of the materials listed above, and may be used for any of the procedures listed herein. The slings are not limited to female urethral support, nor to male urethral support, but may be used in a variety of procedures to support bodily tissues. As mentioned above, multi-layer slings may be fashioned from multiple layers of materials in a variety of techniques in order to strengthen and stiffen the reinforcement.

It is understood that placement of a support or sling in the pelvic floor or under a urethra is a serious operation, with risks of infection and rejection. Accordingly, the sling or support may be impregnated or coated with one or more drugs to resist infection or rejection of the support. The drugs may include rifampin and minocycline, or other antibiotic/antimicrobial drugs. These drugs may include, but are not limited to, a mixture of rifampin and minocycline, a non-steroidal anti-inflammatory agent, a penicillin, a cephalosporin, a carbepenem, a beta-lactam, an antibiotic, a macrolide, a lincosamide, an aminoglycoside, a glycopeptide, a tetracyline, a chloramphenicol, a quinolone, a fucidin, a sulfonamide, a trimethoprim, a rifamycin, an oxaline, a streptogramin, a lipopeptide, a ketolide, a polyene, an azole, an echinocandin, alpha-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methanamine, aldehydes, azylic acid, rifampycin, silver, benzyl peroxide, alcohols, and carboxylic acids and salts, and silver sulfadiazine. Anti-rejection drugs help to prevent rejection of the transplant by the body. Anti-rejection drugs may include, but are not limited to, neomycin, cyclosporine, prednisone and tacrolimus.

It will be understood that no limitation of the scope of the invention is intended by the above description and drawings, which is defined by the claims below.

What is claimed is:

1. A kit for repairing a pelvic floor, the kit comprising:
a support for placement in tissues of a pelvic floor, the support comprising a central portion, opposite first and second end portions, and two transition portions connecting the central portion with the first and second end portions; and
a length of suture comprising a plurality of barbs periodically disposed thereon, the barbs each comprising one or more arms facing in a single direction from the suture, the length comprising first and second parallel portions of the length of suture woven into the first end portion of the support, wherein each of the first and second portions of the length comprises a plurality of barbs disposed thereon, with the arms from the barbs of the first and second portions of the length each face in substantially the same direction with respect to the support, wherein the support is configured to be secured within the patient with at least some of the arms of the plurality of barbs upon the first end portion of the support interacting with tissue of the patient proximate the support.

2. The kit of claim 1, wherein the support further comprises third and fourth portions of the length of suture disposed upon the second end portion of the support, wherein the arms of the barbs upon the third and fourth portions of the length of suture are each oriented in a second direction substantially opposite from the direction of the arms of the barbs upon the first and second lengths of suture.

3. The kit of claim 1, further comprising at least one needle and a handle for placing the support in a patient.

4. The kit of claim 1, further comprising a sheath covering at least a portion of the support.

5. The kit of claim 1, wherein the support further comprises at least one prophylactic or therapeutic drug.

6. The kit of claim 1, wherein the support further comprises third and fourth portions of the length of suture disposed upon the second end portion of the support, wherein the third and fourth portions of the length each comprise a plurality of barbs disposed thereon, wherein the arms of the barbs disposed upon the third portion are oriented in the same direction as the arms of the barbs upon the first and second lengths while the arms of the barbs upon the fourth portion are each oriented in a second direction substantially opposite from the direction of the arms of the barbs of the first, second, and third portions.

* * * * *